United States Patent [19]
Coates et al.

[11] Patent Number: 5,309,098
[45] Date of Patent: May 3, 1994

[54] NUCLEAR MAGNETIC RESONANCE DETECTION OF GEOLOGIC STRUCTURES

[75] Inventors: George R. Coates; Melvin N. Miller; John C. Bouton, all of Malvern, Pa.

[73] Assignee: Numar Corporation, Malvern, Pa.

[21] Appl. No.: 800,599

[22] Filed: Nov. 27, 1991

Related U.S. Application Data

[63] Continuation-in-part of Ser. No. 701,516, May 16, 1991.

[51] Int. Cl.$^5$ .............................................. G01V 3/00
[52] U.S. Cl. ..................................... 324/303; 324/306
[58] Field of Search ................ 324/303, 306, 307, 309

[56] References Cited

U.S. PATENT DOCUMENTS

| | | | |
|---|---|---|---|
| 3,213,357 | 10/1965 | Brown et al. | 324/303 |
| 4,710,713 | 12/1987 | Taicher et al. | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,728,892 | 3/1988 | Vinegar et al. | 324/303 |
| 4,933,638 | 6/1990 | Kenyon et al. | 324/303 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |

FOREIGN PATENT DOCUMENTS 88305343.1 6/1988 European Pat. Off. .

OTHER PUBLICATIONS

Herrick et al., "Improved Nuclear Magnetism Logging . . . " SPE 8361AL, 1979 (no month avail.).

Miller et al., "Spin Echo Magnetic Resonance Logging . . . " SPE 20561, 1990 (no month avail.).

Timur, "Pulsed NMR Studies . . . " Journal of Petro. Tech, Jun. 1969, pp. 775-786.

Sen et al., "Surface-to-volume ratio, charge density, nuclear magnetic relaxation, and permeability in clay--bearing sandstones," Geophysicas, vol. 55, No. 1 (Jan. 1990), pp. 61-69.

Hull et al., "Field Examples of Nuclear Magnetism Logging," Journal of Petroleum Technology (Aug., 1960).

Setser et al., "Measurement of Remaining Oil Saturation in Northern Michigan Using Nuclear Magnetism Log Data and Pressure Core," Society of Petroleum Engineers-SPE 14276 (Sep. 22-25, 1985).

*Primary Examiner*—Louis Arana
*Attorney, Agent, or Firm*—Pennie & Edmonds

[57] ABSTRACT

An improved system for using nuclear magnetic resonance techniques to obtain information relating to geologic structures. The system of the present invention employs a variable sampling window which increases sampling efficiency by allowing the system to optimize the sampling interval, thereby maximizing the amount of data which can be obtained in a series of data samples.

9 Claims, 4 Drawing Sheets

NUCLEAR MAGNETIC RESONANCE DETECTION OF GEOLOGIC STRUCTURES

CONTINUING APPLICATION DATA

This application is a continuation-in-part of application Ser. No. 07/701,516, filed May 16, 1991.

FIELD OF THE INVENTION

The present invention relates to systems for obtaining quantitative and qualitative measurements of geologic structures. More specifically, the present invention provides an efficient and effective system for using nuclear magnetic resonance techniques for obtaining information relating to geologic structures.

BACKGROUND

As is known, fluid flow properties of porous media have long been of interest in the oil industry. In an article by A. Timur, entitled "Pulsed Nuclear Magnetic Resonance Studies of Porosity, Movable Fluid, and Permeability of Sandstones," in the Journal of Petroleum Technology, Jun. 1969, page 775, it was shown experimentally that NMR methods provide a rapid non-destructive determination of porosity, movable fluid, and permeability of rock formation.

It is known that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter T1, known as the spin-lattice relaxation time.

It has been observed that the mechanism which determines the value of T1 depends on molecular dynamics. In liquids, molecular dynamics are a function of molecular size and inter-molecular interactions. Therefore, water and different types of oil have different T1 values.

In the heterogeneous media, such as a porous solid which contains liquid in its pores, the dynamics of the molecules close to the solid surface are also significant and differ from the dynamics of the bulk liquid. It may thus be appreciated that the T1 parameter provides valuable information relating to well logging parameters.

There exist a number of techniques for disturbing the equilibrium of an assembly of magnetic moments, such as those of hydrogen nuclei, for T1 parameter measurements. Each of these techniques provides means for measuring T1 of a rock formation within a certain volume (called the "sensitive volume") which is determined mainly by the shape of the magnetic field surrounding the magnetic structure. The signal-to-noise ratio of the measurement is limited by the ratio of the sensitive volume to the uniformity (maximum flux density minus minimum flux density) of the magnetic field within said volume, and increases in proportion to this ratio.

In any given nuclear magnetic resonance instrument configuration, the apparatus will respond only to nuclei residing within the sensitive volume. In the present invention and prior art instruments described herein, the boundaries of the sensitive volume are determined by radiation patterns of transmitting and receiving antennae as well as a combination of the detailed structure of the magnetic field with the receiver's frequency passband. The radio frequency that a given nucleus will respond to or emit when excited is proportional to the flux density of the magnetic field in which it is immersed. The proportionality factor depends upon the nuclear species. For hydrogen nuclei, that factor is 42.5759 MHz/Tesla. If the NMR receiver's passband extends from 1.30 MHz to 1.31 MHz, the instrument will be sensitive to hydrogen nuclei in regions of the magnetic field that have flux densities between 30.5 mT and 30.8 mT, providing the antenna radiation pattern allows receiving sufficient signal from that locations.

If it is desired to study nuclei located with a particular region, the magnetic field structure, antenna radiation pattern and receiver passband must all be adjusted to be sensitive to that and only that region. Since the signal-to-noise ratio of the resulting signal is proportional to (among other factors) the square root of the receiver passband width, it is important to minimize the variation of the magnetic field within the desired sensitive volume; smaller variations (better field uniformity) mean a better signal-to-noise ratio. Since the signal-to-noise ratio also increases with increasing frequency, the nominal magnetic field intensity within the volume is also very important. It is immaterial whether this nominal intensity is defined as the central value, average value or some other value within the range of values encompassed by the sensitive volume because only large differences in signal-to-noise ratio are significant.

One technique for measuring T1 of a rock formation is exemplified by what is known as the "Schlumberger Nuclear Magnetic Logging Tool." That tool is described by R. C. Herrick, S. H. Couturie, and D. L. Best in "An Improved Nuclear Magnetic Logging System and Its Application to Formation Evaluation," SPE8361 presented at the 54th Annual Fall Technical Conference and Exhibition of the Society of Petroleum Engineers of AIME, held in Las Vegas, Nev., Sep. 23-26, 1979, and also by R. J. S. Brown et al. in U.S. Pat. No. 3,213,357 entitled "Earth Formation and Fluid Material Investigation by Nuclear Magnetic Relaxation Rate Determination."

The Schlumberger Nuclear Magnetic Logging Tool measures the free precession of proton nuclear magnetic moments in the earth's magnetic field by applying a relatively strong DC polarizing field to the surrounding rock formation in order to align proton spins approximately perpendicularly to the earth's magnetic field. The polarizing field must be applied for a period roughly five times T1 (the spin-lattice relaxation time) for sufficient polarization (approximately two seconds). At the end of polarization, the field is turned off rapidly. Since the protons spins are unable to follow this sudden change, they are left aligned perpendicularly to the earth's magnetic field and precess about this field at the "Larmor Frequency" corresponding to the local earth's magnetic field (roughly from 1300 to 2600 Hz, depending on location).

The spin precession induces in a pick-up coil a sinusoidal signal whose amplitude is proportional to the density of protons present in the formation. The signal decays with a time constant "T2" (transverse relaxation time) due to non-homogeneities in the local magnetic field over the sensing volume.

Improved nuclear magnetic resonance logging tools and methods for using these tools are described generally in U.S. Pat. Nos. 4,710,713; 4,717,876; 4,717,877; and 4,717,878, all of which are commonly owned by the assignee of the present invention. The method and apparatus of the present invention, described in greater detail below, uses the logging tool and techniques described in the above referenced patents to obtain previously unavailable data relating to the composition of a geologic formation. In particular, the system of the present invention uses a variable time window to improve the signal quality obtained from a measurement of a particular formation and to optimize the logging speed of the system.

SUMMARY OF THE INVENTION

The method and apparatus of the present invention provides an improved system for using nuclear magnetic resonance techniques for obtaining information relating to geologic structures. In the system of the present invention, a nuclear magnetic resonance logging tool is used to impart magnetic polarization fields on a portion of a geologic formation. Nuclear magnetic resonance signals from the excited nuclei in the formation are then detected to obtain data for calculating a number of important petrophysical parameters of geologic interest.

The method and apparatus of the present invention provides greater signal to noise ratios for measurements made in shaly-rocks. More specifically, the repeat rate of the measurement, or the logging speed is greatly increased in these shaly-rocks to provide an enhanced signal.

In the method and apparatus of the present invention, a variable time-window echo-recording system is used to obtain significant improvements in signal quality and logging speed. An initial test is performed to provide an assessment of the relaxation qualities of the sample. If the test reveals that the sample is a slow-relaxation rock, then the full time is allocated to measuring echoes. However, if the test reveals that the sample is a fast decay rock, then the echo acquisition time window is reduced. This provides increased efficiency since the system is able to maximize the number of measurements made by optimizing the individual sampling intervals to the particular geologic structure being tested. The system of the present invention is capable of providing additional information relating to the very-fast relaxation rocks where signal levels are typically very low using prior art techniques.

DETAILED DESCRIPTION OF THE PREFERRED EMBODIMENT

Figure 1:
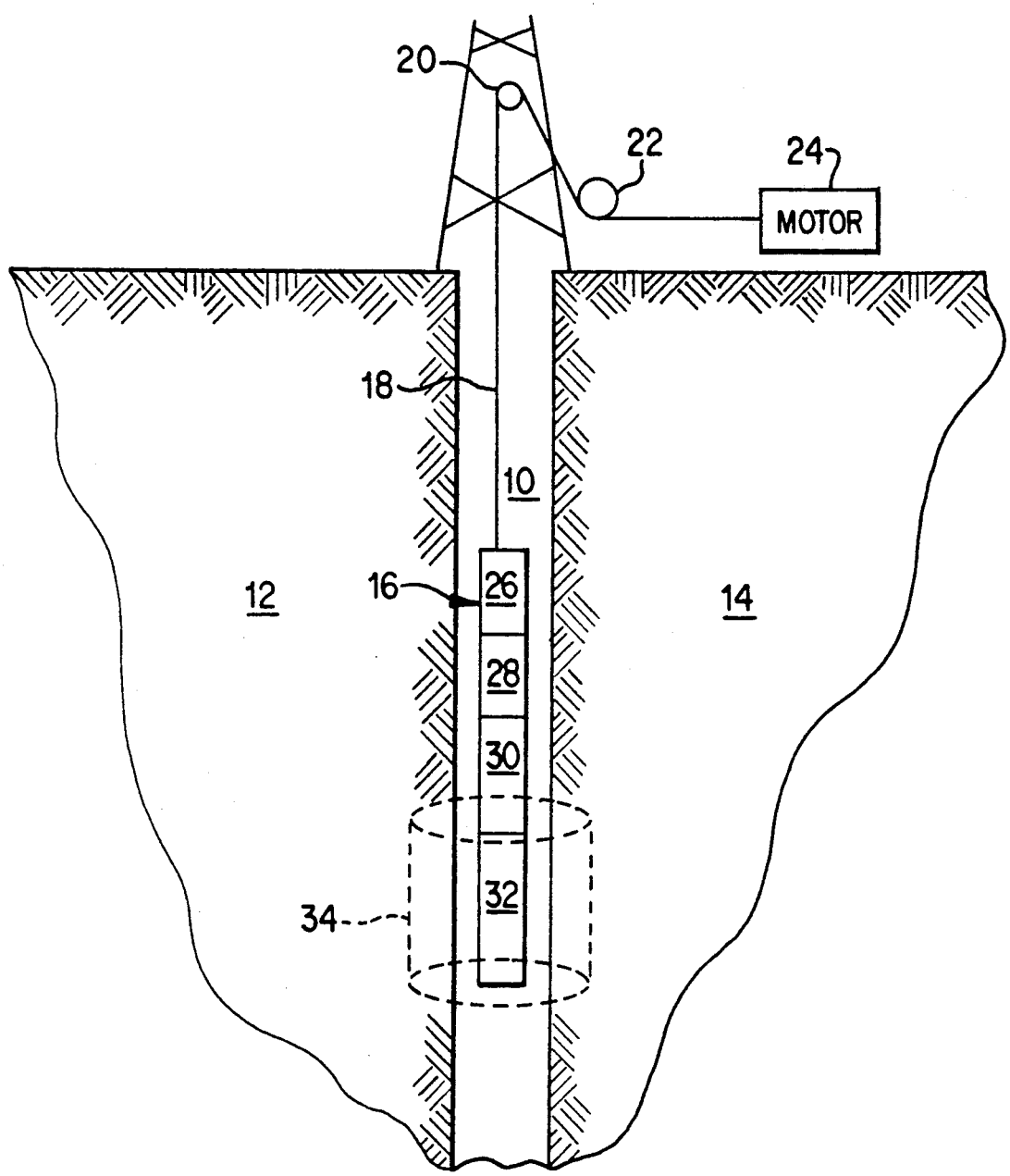
FIG. 1 is a partially pictorial, partially block diagram illustration of a well logging apparatus for obtaining nuclear magnetic resonance measurements of a geologic structure.

Referring to FIG. 1, a borehole 10 is shown adjacent to formations 12 and 14 having structures to be examined using the method and apparatus of the present invention. Within the borehole, there is a logging tool 16 which is suspended by a cable 18 routed over pulleys 20 and 22, with the position of the cable 18 being determined by a motor 24.

The upper portion of the logging tool 16 comprises telemetry electronics 26, gamma ray sensing electronics 28 and magnetic resonance imaging (MRI) electronics 30. A MRI probe 32 is suspended at the bottom of the probe to provide excitation to the surrounding geologic formation. The excitation field has a generally cylindrical shape as represented by reference numeral 34. Improved devices which can be used for the probe 32 are described generally in U.S. Pat. Nos. 4,710,713; 4,717,876; 4,717,877; and 4,717,878, which, by this reference, are incorporated herein for all purposes.

The MRI electronics 30 employed in the system of the present invention comprises both the electronics to control the signals emitted by the MRI probe 32 and detection electronics for receiving the spin-spin pulse-echo signals from the formation being tested. The operation of these components to select an optimized sampling interval will be discussed in greater detail below.

The spin-spin pulse-echo measurement of the spin-echo relaxation of the sample, in a homogenous isotropic media, reflects the surface-to-volume characteristics of the pores. In typical rocks encountered in the well-logging environment, the rocks are complex mixtures of minerals which often include a variety of pore sizes. Consequently, the measured spin-echo relaxation in such an environment is a complex phenomenon, a reflection of the variations which exist in terms of pore surface-to-volume ratios and surface-to-fluid interactions.

The method and apparatus of the present invention is based on the discovery that for a select time window of echo relaxation there is an associated select range of surface-to-volume response. Thus, by proper selection of spin-echo time windows it is possible to determine the relative fraction of select surface-to-volume components. In addition, these changes in relaxation time can also be used as a measure of a representative pore-size condition.

Figure 2:
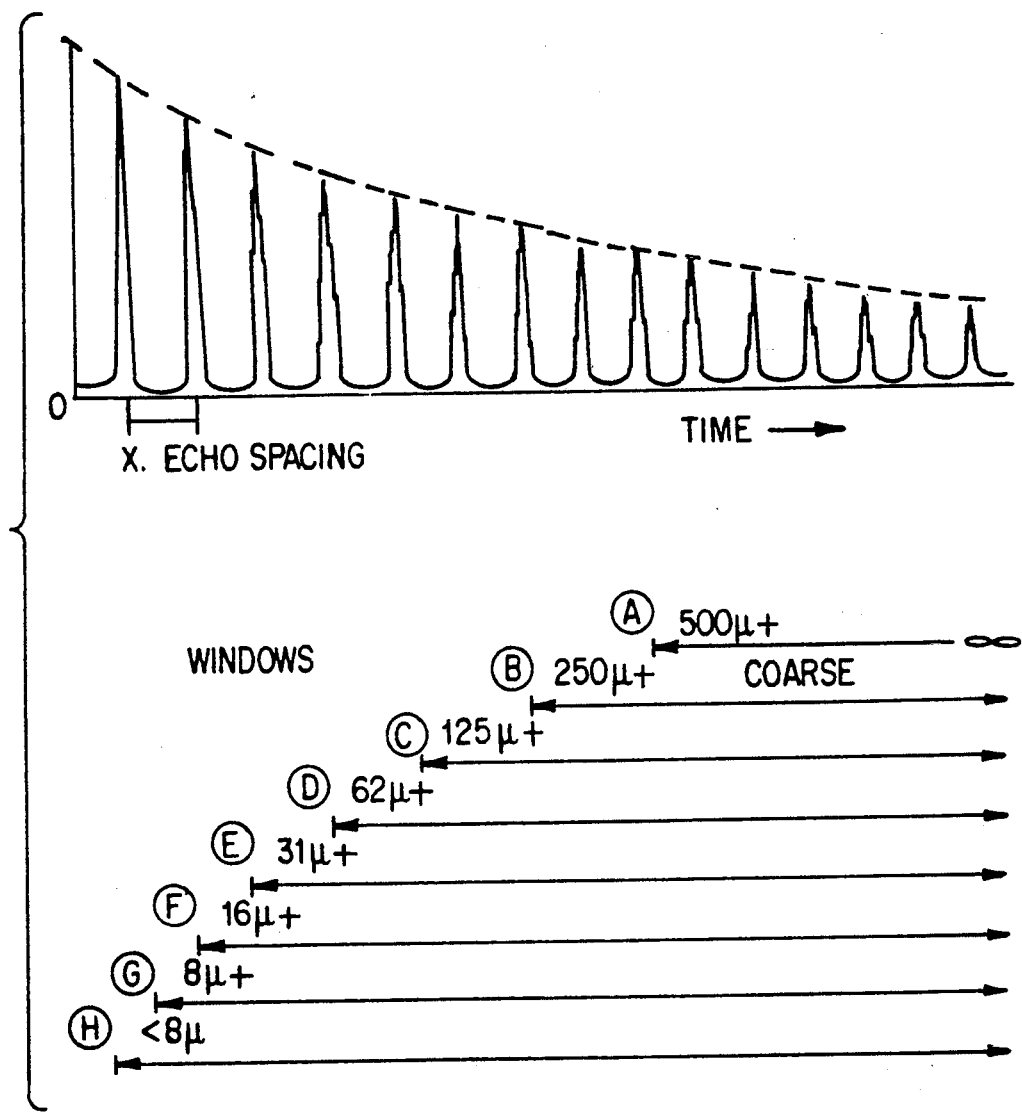
FIG. 2 is a graphical illustration of a chain of spin-echo relaxation signals as a function of amplitude versus time for a geologic structure investigated using a nuclear magnetic resonance system such as that shown in FIG. 1.

FIG. 2 is a graphical illustration of a chain of spin-echo relaxation signals as a function of amplitude versus time for a geologic structure investigated using a nuclear magnetic resonance system such as that shown in FIG. 1. The spacing of the time intervals between the pulses in this application is typically between 1.5 and 3 milliseconds. The time intervals labelled "A-H" correspond to the signal intervals for various particle sizes, with interval "A" corresponding to the interval for particles larger than 500$\mu$ and interval "H" corresponding to the interval for particles of larger than 8$\mu$, etc.

The calibration of the process is accomplished through multi-dimension regression analysis utilizing optimally selected and prepared laboratory samples. Such regression techniques are known to those skilled in the art and are described in the following references: K. Fukunaga, *Introduction to Statistical Pattern Recognition*, Academic Press, 1972; Bhattacharyya & Johnson, *Statistical Concepts and Methods*, Wiley & Sons, 1977;

and Devijver & Kittler, *Pattern Recognition—A Statistical Approach*, Prentice Hall, 1982.

In the present invention, the transmitter activation and echo-recordings are normally synchronized to ensure the full spectrum of $T_2$ relaxation is accomplished (typically 300 msecs). The technique is typically calibrated to the slowest relaxation condition since these constitute the best reservoir pore-size condition.

However, in most well-bores, the vast majority of the formations are comprised of very-fine pore structures associated with the shale and shaly-sand formations. Since the recording interval is typically the full 300 msec, the repeat rate of the measurement, and thus the logging speed is greatly reduced in these shaly-rocks.

Figure 3A:
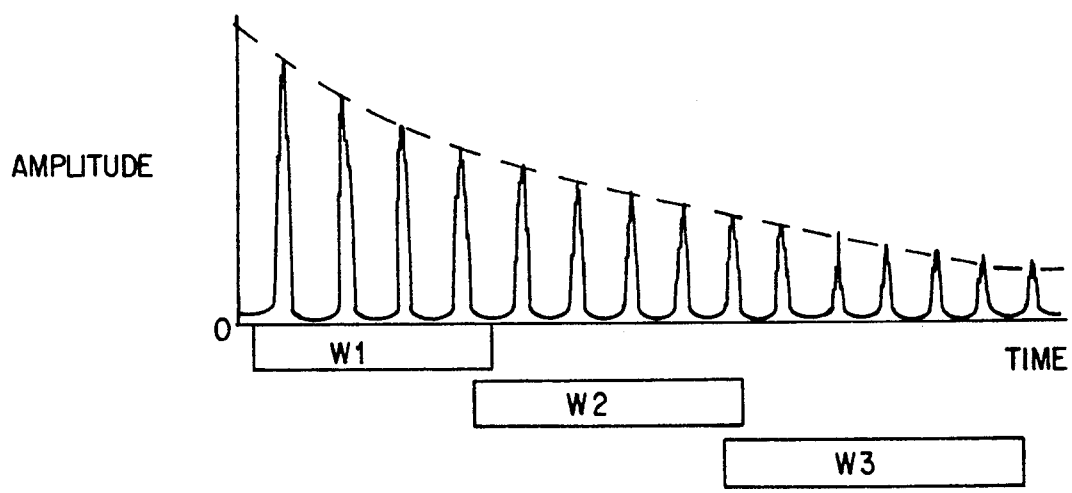
FIG. 3a is a graphical illustration of time interval windows which can be used to determine the amplitude decay characteristics of the sample in accordance with the method and apparatus of the present invention.
Figure 3B:
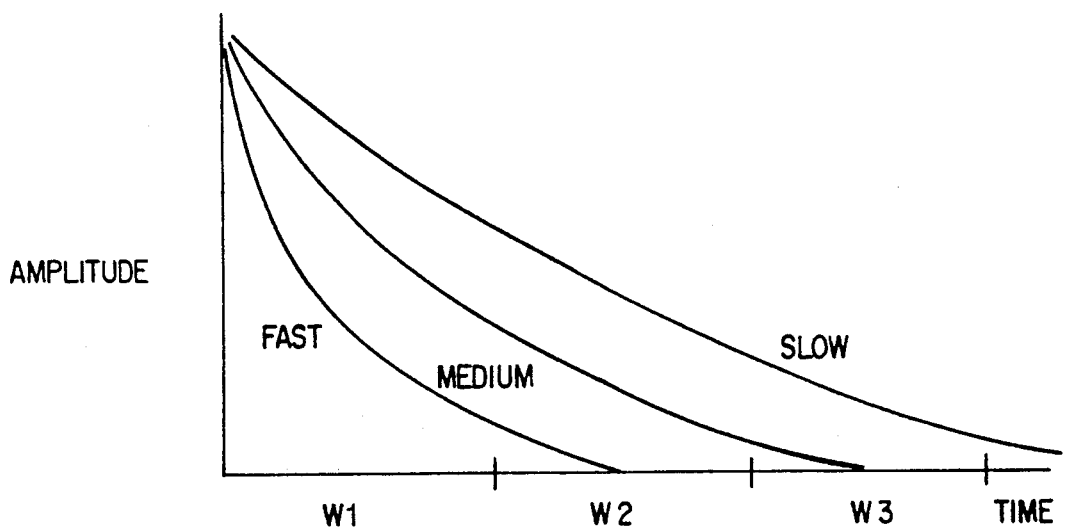
FIG. 3b is an illustration of the relative slope of a sample having a fast relaxation time and a sample having a slow relaxation time.

The method and apparatus of the present invention employs a variable time-window echo-recording system which provides significant improvements in signal quality and logging speed. FIG. 3a is a graphical illustration of a chain of spin-echo relaxation signals as a function of amplitude versus time for a particular geologic structure. The slope of the pulse amplitude curve is characteristic of the particular geologic formation being tested. FIG. 3b is an illustration of the possible slopes for pulse amplitude curves corresponding to a fast decay (very fine pore formation), medium decay (medium pore formation), and slow decay (reservoir-type pore formation). The time intervals $w_1$, $w_2$, and $w_3$ correspond to the sampling intervals which would optimize the collection of spin-echo pulse information relating to the respective geologic composition of a formation. For example, the time window $w1$ is the time interval which optimizes the collection of data relating to very-fine pore structures. Likewise the time intervals $w_2$, and $w_3$ are the time intervals for optimizing the collection of data relating to medium and large pore structures, respectively.

In the present invention, an initial test is performed to determine the relaxation characteristics of the formation being tested. The information obtained from this initial test is then used to select a sampling interval which optimizes the collection of data for the particular pore structure of the formation being tested.

Figure 4:
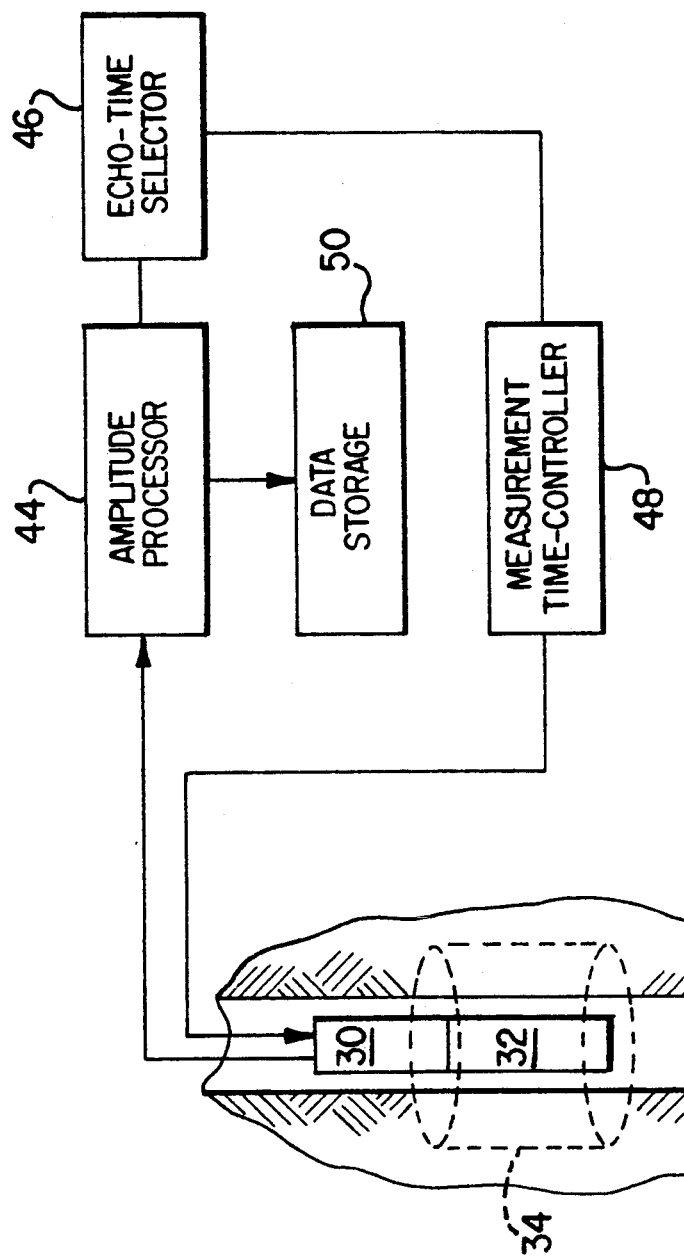
FIG. 4 is a block diagram illustration of the components for controlling the echo acquisition time window in the system of the present invention.

FIG. 4 is a block diagram of the components used to control the data collection interval in the system of the present invention. The MRI electronics 30 comprises an MRI probe controller and pulse echo detection electronics. As was discussed above, an initial test is conducted to determine the relaxation characteristics of the sample. This is accomplished by a full 300 msec test cycle. The output signal from the detection electronics is processed by the amplitude processor 44 to obtain an initial regression analysis of the relaxation characteristics of the sample. The output of the amplitude processor 44 is provided to the echo time selector 46 which selects the optimum sampling time interval. This time interval is implemented by the measurement cycle controller 48 which provides an appropriate control signal to the MRI probe controller. Once the sampling interval has been selected, the repeated data samples are obtained and processed by the amplitude processor 44, with the processed data being stored in data storage 50.

If the initial data indicates that the sample has slow-relaxation characteristics, then the full sampling interval (e.g., 300 msec) is maintained for subsequent samples. However, if the initial data indicates that the formation has fast relaxation characteristics, then a shorter sampling interval (e.g., 50–100 msec) is used for subsequent data acquisition. This reduction in the sampling interval time window allows the system to obtain additional measurements in the same amount of time which would otherwise be required for a single measurement. These additional measurements are especially useful for analyzing formations having very fast relaxation characteristics for which signal levels are typically very low. The system of the present invention, therefore, has the advantage of providing improved measurements of fast decay formations, while maintaining the current signal-to-noise qualities in the slow relaxation rocks.

Although the present invention has been described in connection with the preferred embodiment, it is not intended to be limited to the specific form set forth herein, but on the contrary, it is intended to cover such modifications, alternatives, and equivalents as can be reasonably included within the spirit and scope of the invention as defined by the appended claims.

I claim:

1. A method for determining the optimum sampling interval for measurement of parameters related to the composition of a geologic structure, comprising the steps of:
   (a) imparting a polarizing magnetic field to a geologic structure for a predetermined period of time;
   (b) repeatedly exciting the nuclei of a population of particles in said geologic structure with an RF field;
   (c) measuring repeatedly during a first time interval nuclear magnetic resonance echo signals of said population of particles in said geologic structure so as to acquire a chain of echo signals; and
   (d) determining from said chain of echo signals an optimum sampling interval for obtaining a plurality of subsequent data measurements relating to said geologic structure.

2. The method according to claim 1 wherein the step of determining includes the step of performing a regression analysis of said chain of echo signals to determine the relaxation characteristics of said geologic structure.

3. The method according to claim 1, said first time interval for measuring said nuclear magnetic resonance signals being approximately 300 milliseconds.

4. The method according to claim 1, further comprising the step of obtaining a plurality of subsequent data measurements relating to said geologic structure, said subsequent data measurements comprising a plurality of chains of echo signals obtained using said optimum sampling interval.

5. A method for determining the optimum sampling interval for measurement of parameters related to the composition of geologic structure, comprising the steps of:
   (a) imparting a polarizing magnetic field to a geologic structure for a predetermined period of time;
   (b) repeatedly exciting the nuclei of a population of particles in said geologic structure with an RF field;
   (c) measuring repeatedly during a first time interval echo signals of said population of particles in said geologic structure so as to acquire a chain of echo signals;
   (d) performing a regression analysis of said chain of echo signals to determine the relaxation characteristics of said geologic structure;
   (e) using said regression analysis to determine an optimum sampling interval for obtaining subsequent nuclear magnetic resonance measurements of said geologic structure; and (f) obtaining a plurality of subsequent data measurements relating to said geologic structure, said subsequent data measurements comprising a plurality of chains of echo signals obtained using said optimum sampling interval.

6. The method according to claim 5, said optimum sampling interval being less than or equal to said first time interval.

7. The system according to claim 6, said first time interval being approximately 300 milliseconds.

8. An apparatus for determining the optimum sampling interval for measurement of parameters related to the composition of a geologic structure, comprising:

means for imparting a polarizing magnetic field to a geologic structure for a predetermined period of time;

means for repeatedly exciting the nuclei of a population of particles in said geologic structure with an RF field;

means for measuring repeatedly during a first time interval echo signals of said population of particles in said geologic structure so as to acquire a chain of echo signals; and means for determining from said chain of echo signals an optimum sampling interval for obtaining data relating to said geologic structure.

9. The apparatus according to claim 8, wherein the means for determining includes means for performing a regression analysis of said chain of echo signals to determine the relaxation characteristics of said geologic structure.

* * * * *